(12) United States Patent
Shalaby et al.

(10) Patent No.: US 8,585,772 B2
(45) Date of Patent: Nov. 19, 2013

(54) ABSORBABLE/BIODEGRADABLE COMPOSITE YARNS AND PROPERTY-MODULATED SURGICAL IMPLANTS THEREFROM

(75) Inventors: Shalaby W Shalaby, Anderson, SC (US); Shawn J Peniston, Easley, SC (US)

(73) Assignee: Poly-Med, Inc., Anderson, SC (US)

( * ) Notice: Subject to any disclaimer, the term of this patent is extended or adjusted under 35 U.S.C. 154(b) by 1248 days.

(21) Appl. No.: 11/886,370

(22) PCT Filed: Apr. 20, 2006

(86) PCT No.: PCT/US2006/014939
§ 371 (c)(1),
(2), (4) Date: Sep. 14, 2007

(87) PCT Pub. No.: WO2006/116000
PCT Pub. Date: Nov. 2, 2006

(65) Prior Publication Data
US 2009/0024151 A1    Jan. 22, 2009

Related U.S. Application Data

(60) Provisional application No. 60/674,826, filed on Apr. 26, 2005.

(51) Int. Cl.
*A61F 2/02* (2006.01)

(52) U.S. Cl.
USPC .................................................... 623/23.72

(58) Field of Classification Search
USPC ........... 606/151, 213; 623/2.36, 23.72–23.76, 623/22.33; 600/37; 604/285, 304; 602/41–44; 87/12; 977/767
See application file for complete search history.

(56) References Cited

U.S. PATENT DOCUMENTS

| | | | |
|---|---|---|---|
| 5,143,082 A | | 9/1992 | Kindberg et al. |
| 6,319,264 B1 * | | 11/2001 | Tormala et al. ............... 606/151 |
| 6,350,284 B1 | | 2/2002 | Tormala et al. |
| 6,398,814 B1 | | 6/2002 | Paasimaa et al. |
| 2002/0120291 A1 | | 8/2002 | Shalaby |

FOREIGN PATENT DOCUMENTS

| | | |
|---|---|---|
| WO | 9951163 A1 | 10/1999 |
| WO | 2004028583 A2 | 4/2004 |

* cited by examiner

*Primary Examiner* — Melanie Tyson
(74) *Attorney, Agent, or Firm* — McCormick, Paulding & Huber LLP

(57) ABSTRACT

Absorbable/biodegradable composite yarns contain at least two types of fibrous components having distinctly different absorption and strength retention profiles and are useful in constructing surgical implants, such as sutures and meshes with integrated physicochemical and biological properties, wherein these properties are modulated through varying the individual yarn content and controlling the geometry of these constructs.

24 Claims, No Drawings

ABSORBABLE/BIODEGRADABLE COMPOSITE YARNS AND PROPERTY-MODULATED SURGICAL IMPLANTS THEREFROM

This application claims priority to PCT Application No. PCT/US2006/014939 filed Apr. 20, 2006, which claims the benefit of Provisional application Ser. No. 60/674,826 filed Apr. 26, 2005, all of which are incorporated herein in their entirety.

FIELD OF THE INVENTION

This invention is directed to absorbable/biodegradable composite yarns having at least two fibrous components with distinctly different individual physicochemical and biological properties for use in constructing absorbable/biodegradable medical devices or surgical implants, such as sutures, meshes, and allied textile constructs, displaying a gradient in clinically relevant properties.

BACKGROUND OF THE INVENTION

Blending of non-absorbable fibers having distinctly different individual physicochemical properties is a well-established practice in the textile industry and is directed toward achieving unique properties based on the constituent fibers in such blends. The most commonly acknowledged examples of these blends include combinations of (1) wool staple yarn and polyethylene terephthalate (PET) continuous multifilament yarn to produce textile fabrics which benefit from the insulating quality of wool and high tensile strength of the polyester; (2) cotton staple yarn and PET continuous multifilament yarn to produce water-absorbing, comfortable (due to cotton), strong (due to PET) fabrics; (3) nylon continuous multifilament yarn and cotton staple yarn to achieve strength and hydrophilicity; and (4) cotton staple yarn and polyurethane continuous monofilament yarn to yield water-absorbing, comfortable elastic fabrics. The concept of blending non-absorbable and absorbable fibers was addressed to a very limited extent in the prior art relative to combining PET with an absorbable polyester fiber in a few fibrous constructs, such as hernial meshes and vascular grafts, to permit tissue ingrowth in the PET component, as the absorbable fibers lose mass with time. Similar combinations were investigated with polypropylene and absorbable polyester in hernial meshes and vascular grafts. However, the use of totally absorbable/biodegradable blends of two or more yarns to yield fibrous properties that combine those of the constituent yarns is heretofore unknown in the prior art. This provided the incentive to pursue this invention, which deals with totally absorbable/biodegrade-able composite yarns having at least two fibrous components and their conversion to medical devices, such as sutures and meshes, with modulated, integrated physicochemical and biological properties derived from the constituent yarns and which can be further modified to exhibit specific clinically desired properties.

SUMMARY OF THE INVENTION

Accordingly, the present invention is directed to an absorbable/biodegradable surgical implant formed of at least two differing fibrous components, the differing components having differing absorption profiles and differing strength retention profiles in the biological environment.

In one preferred embodiment the fibrous components of the implant are plied multifilament yarns of at least two individual continuous yarns, each yarn formed from a polyester made from at least one monomer selected from glycolide, lactide, ε-caprolactone, trimethylene carbonate, p-dioxanone, 1,5-dioxepan-2-one, and a morpholine-2,5-dione. Preferably, the polyester is a segmented/block copolymer having sequences derived from at least one monomer selected from glycolide-, l-lactide, trimethylene carbonate, and caprolactone.

In another embodiment the fibrous components are plied multifilament yarns, at least one of which is formed from a synthetic polyester copolymer and a biosynthetic polyhydroxyalkanoate. Alternatively, the fibrous components are plied multifilament yarns wherein at least one of the plied multifilament yarns is formed of a synthetic polyester and at least one of the plied multifilament yarns is formed of a biosynthetic polyhydroxyalkanoate.

The present absorbable/biodegradable surgical implant can be any of a variety of medical devices such as, for example, a braided suture, a knitted mesh construct for use in hernial repair, of a woven mesh construct. Specifically, the fibrous components may comprise individual yarns which are plied, braided and subsequently knitted or woven into a mesh construct. Both sutures and meshes may include a surface coating in accordance with the present invention. In the case of sutures the coating may be an absorbable polymer to improve tie-down properties and minimize tissue drag. Similarly for meshes, whether knitted or woven, an absorbable polymer surface coating may be employed to modulate the construct permeability to biological fluids and tissue ingrowth into the construct.

Absorbable/biodegradable sutures in accordance with the present invention may comprises a core derived from a first type of yarn and a sheath derived from a second, differing type of yarn.

Other absorbable/biodegradable medical devices in accordance with the present invention include a device for use as a tissue-engineered hernial repair patch, or a device for use as a tendon, ligament, or vascular graft. Further the present absorbable/biodegradable implant can be a tubular knitted mesh which may include a thin absorbable film insert. Preferably such mesh and film insert are provided in the form of a compressed, three-layer sheet construct for use in hernial repair. Most preferably the three-layer sheet construct further includes an absorbable coating.

Regardless of the form taken by the present inventive absorbable/biodegradable surgical implant, it may preferably include an absorbable polyester coating which contains a bioactive agent selected from antimicrobial agents, analgesic agents, antineoplastic agents, anti-inflammatory agents, and cell growth promoters.

In yet another preferred embodiment fibrous components of the present surgical implant are at least two differing yarns, at least one of which is a multifilament and at least one of which is a monofilament yarn, each yarn formed of a different polyester made from at least one monomer selected from glycolide, l-lactide, ε-caprolactone, p-dioxanone, trimethylene carbonate, 1,5-dioxepan-2-one, and a morpholinedione, by ring-opening polymerization in the presence of an organometallic catalyst and an organic initiator. Preferably this arrangement is used in forming a coated or uncoated jersey knit mesh, a coated or uncoated warp knit mesh, a coated or uncoated woven mesh, a device for hernial repair, vascular tissue repair, producing vascular grafts or tissue engineering, or a coated or uncoated suture comprising a monofilament core and a braided sheath. This arrangement benefits from a coating of an absorbable polyester having a melting temperature of less than 100° C., which preferably contains at least one bioactive agent selected from antimicrobial agents, anti-inflammatory agents, antineoplastic agents, anesthetic agents, and growth promoting agents.

DETAILED DESCRIPTION OF PREFERRED EMBODIMENTS

The clinical need for synthetic absorbable sutures, which elicit minimum tissue response in biological tissues, was acknowledged over four decades ago. Since then, the demand for many forms of absorbable fibrous constructs has grown consistently as the surgical procedures have become more sophisticated and contemporary surgeons voice demands for more site-specific, highly effective surgical sutures and allied products, particularly meshes. For totally absorbable/biodegradable sutures and meshes, the clinical community is quite ready to exploit a new aspect in these devices that is associated with modulated physicochemical and biological properties, which, in turn, permit the prolonged use of these devices over longer periods at progressively healing and remodeling the biological sites. Additionally, modulated absorption and incremental degradation minimize the risk of uncontrolled production of acidic by-products. This, in turn, results in minimized tissue reaction during the use period. To meet such a challenge, the present invention uses specific combinations of short- and long-term absorbable yarns to produce composite devices that meet a broad range of tissue repair requirements.

In cases of absorbable sutures, instead of having a polyglycolide (PGA) suture that loses its wound-holding capacity in about three weeks, a yarn composite of PGA-based yarn and copolymeric high lactide-based yarn will provide a progressive loss in holding capacity over a period of 1 to 12 weeks. This allows a prolonged healing period and gradual transfer of load from the suture to the biological tissue over 1 to 12 weeks, which can be imperative for geriatric and diabetic patients as well as patients with other types of compromised wounds. Braided, knitted, and woven constructs made of certain composite yarns exhibit lower values for their modulus than would be expected upon averaging the modulus values of the corresponding constituent single-yarn constructs.

The woven and/or knitted meshes made of absorbable/biodegradable composite yarn, subject of this invention, are designed for use in applications associated with (1) genital prolapse and stress continence in women; (2) unilateral hernia repair; (3) reconstruction of the diaphragm in extensive congenital hernia; (4) several types of laparoscopic hernia repairs; (5) preventing parastromal hernia, a common complication following colostomy; (6) inguinal and incisional hernia repair; (7) abdominal wall hernia; (8) enlargement of the right ventricular outflow tract; (9) femoral hernia; (10) umbilical hernia; (11) epigastric hernia; and (12) incisional or ventral hernia. In all these projected applications of the meshes, subject of this invention, the totally absorbable/biodegradable composite meshes with modulated absorption and strength retention profiles should be favored over commercially available non-absorbable ones made primarily of Teflon®, polypropylene, and polyethylene terephthalate for the following reasons:

(1) The ability of the composite mesh to provide a site-specific mechanical support for prescribed periods of time, because of its exceptionally broad range of strength retention profiles;

(2) The ability of the composite mesh to transfer the load gradually to the surrounding tissue concomitant with gradual decay of the mesh mechanical strength. This, in turn, contributes to the acceleration of repair of the surrounding tissue;

(3) As the composite mesh undergoes gradual mass loss, the surrounding tissue is allowed to regrow and retain its natural shape at the surgical site;

(4) Since the composite mesh is transient, the incidence of long-term infection is practically non-existent following the repair of the tissue in question.

To satisfy specific bioengineering and clinical needs, in one aspect the present invention is directed to composite fibrous constructs wherein at least one of the constituent fibers or yarns is a monofilament that is responsible for increasing the construct initial rigidity, and at least one constituent fiber or yarn is a multifilament which is responsible for increasing the surface area and porosity of said composite construct. The monofilament polymeric material is selected to differ from that of polymeric material used to produce the multifilament, so as to provide a construct which displays practically biphasic or multiphasic absorption and strength retention profiles in the biological environment. The monofilament and multifilament yarn combinations can be used to produce (1) jersey knit surgical mesh following using a standard tube or flat-knitting process; (2) warp knit surgical mesh that can be cut into smaller sizes to match the area of the surgical site without unraveling; and (3) surgical sutures which may have a monofilament core of a single strand or multiple strand of up to five monofilaments and a sheath of a multifilament yarn. In certain forms, the monofilament and multifilament yarns may be used as sheath and core, respectively. From a clinical perspective, the surgical mesh comprising the monofilament and multifilament yarns (whether jersey or warp knit mesh) can be used as such for hernial repair, vascular graft, vascular patch, or tissue engineering. Alternatively, the mesh can be coated with an absorbable coating to (1) modulate the mesh absorption and strength retention profiles in the biological environment; (2) function as a surface lubricant to facilitate handling and improve suturability at the surgical site; and (3) be used as a matrix for the controlled release of at least one bioactive agent. Likewise, a suture construct comprising a monofilament and multifilament yarn can be used as such or as a coated article wherein the coating is expected to (1) modulate the suture absorption and strength retention profile in the biological environment; (2) function as a surface lubricant to optimize the suture frictional properties and facilitate its tie-down during knot formation and (3) be used as matrix for the controlled delivery of at least one bioactive agent.

Further illustrations of the present invention are provided by the following examples:

EXAMPLE 1

Preparation of High Glycolide- and High Lactide-based Copolymers

Two high glycolide-based copolymers, P1 and P2, and two high lactide-base copolymers, P3 and P4, were prepared as outlined below:

Preparation of P1: A 95/5 (molar) mixture of glycolide/l-lactide was polymerized under traditional ring-opening polymerization using stannous octanoate as a catalyst and 1-decanol as the initiator at a maximum polymerization temperature of 220° C. until practically complete conversion was achieved. The polymer was isolated, ground, dried, and residual monomers were removed by distillation under reduced pressure. The purified polymer was characterized for identity and composition (IR and NMR), thermal properties (DSC), and molar weight (inherent viscosity in hexafluoro isopropyl alcohol, HFIP).

Preparation of P2: A mixture of 95/5 (molar) glycolide/ε-caprolactone was end-grafted onto polyaxial polytrimethylene carbonate as a polymeric initiator to produce P2, using similar conditions to those disclosed in U.S. Pat. Nos. 6,498,229 and 6,462,169, each hereby incorporated herein by reference, for preparing the polymeric polyaxial initiator and completing the end-grafting scheme, respectively. The polymer was isolated, ground, dried, purified, and characterized as described for P1.

Preparation of P3: The copolymer was prepared using 88/12 (molar) l-lactide/tri-methylene carbonate as per the teaching of U.S. Pat. No. 6,342,065. The polymer was isolated, ground, dried, purified, and characterized as described for P1 above with the exception of using chloroform as a solvent for the solution viscosity measurement.

Preparation of P4: The copolymer was prepared using 84/11/5 (molar) l-lactide/tri-methylene carbonate/caprolactone as per the teaching of U.S. Pat. No. 6,342,065. The polymer was isolated, ground, dried, purified, and characterized as described for P3.

EXAMPLE 2

Preparation of Monofilament and Multifilament Yarns for Braiding and Knitting

General Method

To produce the monofilament or multifilament yarns, the specific polymer was melt-spun using a ¾" extruder equipped with a single or 20-hole die, respectively, following the general protocol described in U.S. Pat. No. 6,342,065. The extruded yarn was oriented during a two-stage drawing using a series of heated Godets.

EXAMPLE 3

Preparation of Coreless Braid

General Method

For preparing the coreless braids of a single multifilament yarn, a 16-carrier braider, loaded with the specific yarn, was used. The resulting braids were then annealed at 80° C. for one hour at a constant length. For the braids based on composite yarn, the 16-carrier braider was loaded with two or more types of individual yarns. The resulting braids were annealed for one hour at 80° C. at a constant length.

EXAMPLE 4

Preparation and Testing of Tensile Properties of Coreless Braids Made of Single

Component (B1 to B4) and Composite Yarns (B5 to B8) Annealed braids B1 to B4 were made from single-component yarns that have been prepared as described in Example 1 using the copolymeric compositions P1 to P4 described in Table I. Similarly annealed braids B5 to B8 were made from composite yarns, as described in Example 2 using combinations of the individual yarns derived from copolymeric composition P1 to P4. The initial tensile properties of the braids B1 to B8 were measured using an MTS-MiniBionix Universal Tester, Model 858, and tensile data are summarized in Table I.

TABLE I

Composition of the Multifilament Yarns Used for Braiding and Tensile Properties of Braided Sutures Therefrom

| Yarn Composition & Braid Properties | | B1 | B2 | B3 | B4 | B5 | B6 | B7 | B8 |
|---|---|---|---|---|---|---|---|---|---|
| Yarn Composition | | | | | | | | | |
| % of yarn derived from | P1 | 100 | — | — | — | 50 | — | — | 25 |
| | P2 | — | 100 | — | — | — | 50 | 50 | 25 |
| | P3 | — | — | 100 | — | — | 50 | — | — |
| | P4 | — | — | — | 100 | 50 | — | 50 | 50 |
| Braid Properties | | | | | | | | | |
| Diameter mm | | 0.29 | 0.26 | 0.26 | 0.27 | 0.30 | 0.26 | 0.26 | 0.27 |
| Max. load, N | | 38.4 | 29.5 | 28.6 | 31.5 | 31.6 | 23.3 | 28.6 | 29.9 |
| Strength, Kpsi | | 84 | 81 | 78 | 80 | 65 | 64 | 78 | 76 |
| Modulus, Kpsi | | 1016 | 1013 | 744 | 633 | 453 | 845 | 828 | 721 |
| Elongation, % | | 22 | 21 | 46 | 34 | 31 | 23 | 27 | 32 |

EXAMPLE 5

Determination of the In Vitro Breaking Strength Retention (BSR) Profile of Braids B1 to B8

Braids B1 to B8 of Example 4 were incubated (or aged) in a buffered phosphate solution having a pH of 7.2 at 37° C. or 50° C. for a predetermined length of time. At the conclusion of each study period, the individual suture was removed from the phosphate buffer and tested for breaking strength, after removal of excess surface moisture. Using the initial breaking strength of the individual suture as a base line, the determined breaking strength values of the aged sample were used to calculate percent BSR. The BSR results are summarized in Table II. The results show that braids made of composite yarns do exhibit BSR profiles that range between those of the individual constituent components.

TABLE II

In Vitro Breaking Strength Retention (BSR) of Braided Sutures

| BSR Data | Braid Number: | | | | | | | |
|---|---|---|---|---|---|---|---|---|
| | B1 | B2 | B3 | B4 | B5 | B6 | B7 | B8 |
| 37° C. BSR, % at | | | | | | | | |
| Day 6 | 81 | 65 | — | 91 | 66 | 61 | 66 | 57 |
| Day 8 | 63 | 48 | 83 | 87 | 52 | 53 | 53 | — |
| Day 10 | 48 | 32 | 82 | — | 44 | — | — | — |
| Week 2 | 12 | 0 | 78 | 86 | 43 | 49 | 52 | 52 |
| Week 3 | 0 | — | 73 | — | 45 | 43 | — | — |
| Week 4 | — | — | — | 80 | — | — | 54 | 48 |
| 50° C. BSR at | | | | | | | | |
| Day 2 | 53 | 55 | 86 | — | — | 62 | 65 | — |
| Day 4 | 3 | 0 | 82 | 93 | 51 | — | 57 | 52 |
| Day 6 | 0 | — | — | — | — | 52 | 56 | — |

TABLE II-continued

In Vitro Breaking Strength Retention (BSR) of Braided Sutures

| BSR Data | Braid Number: | | | | | | | |
|---|---|---|---|---|---|---|---|---|
| | B1 | B2 | B3 | B4 | B5 | B6 | B7 | B8 |
| Day 8 | — | — | 75 | 90 | 46 | 46 | 56 | 49 |
| Week 2 | — | — | 63 | 89 | 46 | 41 | 52 | 47 |
| Week 3 | — | — | 56 | 81 | 42 | 32 | 49 | 44 |
| Week 4 | — | — | — | 77 | 38 | 28 | 44 | 43 |

EXAMPLE 6

Preparation of Knitted Tubular Meshes of Single Component (M1 to M4) and Composite (M5 to M8) Yarns Individual yarns made from copolymers P1 to P4 were prepared as described in Example 1. For preparing knits of one type yarn, individual yarns of P1 to P4 were plied and constructed into a tubular knitted mesh using a circular knitting machine, yielding meshes M1 to M4. The knitted meshes were then annealed at constant length at 80° C. or 95° C. for one hour to yield M1a to M4a, or M1b to M4b, respectively. For preparing the knitted tubular meshes with composite yarns, different combinations of yarns derived from of P1 to P4 were plied and used. The resulting composite yarns were converted, annealed, knitted into tubular meshes M5a to M8a or M5b to M8b, which have been annealed at 80° C. or 95° C., respectively. Table III outlines the composition, preparation conditions, and properties of all meshes.

TABLE III

Composition of the Multifilament Yarns Used for Knitting and Tensile Properties of Knitted Tubular Meshes Therefrom

| Yarn Composition and Mesh Properties | | Mesh Number: | | | | | | | |
|---|---|---|---|---|---|---|---|---|---|
| | | M1 | M2 | M3 | M4 | M5 | M6 | M7 | M8 |
| Yarn Composition | | | | | | | | | |
| % of yarn derived from | P1 | 100 | — | — | — | 50 | — | — | 25 |
| | P2 | — | 100 | — | — | — | 50 | 50 | 25 |
| | P3 | — | — | 100 | — | — | 50 | — | — |
| | P4 | — | — | — | 100 | 50 | — | 50 | 50 |
| Mesh Properties of Set "a" Annealed at 80° C. | | M1a | M2a | M3a | M4a | M5a | M6a | M7a | M8a |
| Equivalent Diameter, mm | | 1.42 | 1.47 | 1.4 | 1.09 | 1.22 | 1.52 | 1.27 | 1.27 |
| Max. load, N | | 155.4 | 199.5 | 97.4 | 81.9 | 93.0 | 139.4 | 113.9 | 107.5 |
| Breaking Strength, Kpsi | | 14 | 17 | 9 | 13 | 12 | 11 | 13 | 12 |
| Modulus, Kpsi | | 41 | 64 | 63 | 80 | 47 | 66 | 66 | 52 |
| Elongation, % | | 72 | 53 | 50 | 42 | 42 | 42 | 42 | 43 |
| Mesh Properties of Set "b" Annealed at 95° C. | | M1b | M2b | M3b | M4b | M5b | M6b | M7b | M8b |
| Equivalent Diameter, mm | | 1.36 | 1.36 | 1.36 | 1.11 | 1.19 | 1.41 | 1.23 | 1.2 |
| Max. load, N | | 169.0 | 226.8 | 109.6 | 76.5 | 98.7 | 139.0 | 117.1 | 111.0 |
| Breaking Strength, Kpsi | | 17 | 23 | 11 | 12 | 13 | 13 | 14 | 14 |
| Modulus, Kpsi | | 68 | 99 | 84 | 83 | 81 | 71 | 93 | 86 |
| Elongation, % | | 64 | 51 | 47 | 39 | 39 | 39 | 36 | 36 |

EXAMPLE 7

Determination of the In Vitro Breaking Strength Retention (BSR) Profiles of the Knitted Meshes This was conducted at pH 7.2 and 37° C. or 50° C. as described earlier for the braided yarn. The BSR results are summarized in Table IV. The results show that knitted tubular meshes made of composite yarns do exhibit BSR profiles that range between those made from the individual constituent components, in a similar manner as discussed in Example 5 for their braid counterparts.

TABLE IV

In Vitro Breaking Strength Retention (BSR) of Knitted Tubular Meshes

| BSR Data | Mesh Number: Set "a" | | | | | | | |
|---|---|---|---|---|---|---|---|---|
| | M1a | M2a | M3a | M4a | M5a | M6a | M7a | M8a |
| 37° C. BSR, % at | | | | | | | | |
| Day 6 | 33 | 70 | 99 | 90 | 70 | 74 | 83 | 70 |
| Day 8 | 17 | 49 | 101 | 96 | 39 | 59 | 59 | 46 |
| Day 10 | 5 | 30 | 102 | 97 | 31 | 39 | 35 | 28 |
| 50° C. BSR at | | | | | | | | |
| Day 2 | 22 | 59 | 99 | 95 | 68 | 75 | 86 | 81 |
| Day 4 | 0 | 6 | 106 | 95 | 31 | 33 | 23 | 27 |
| Day 6 | — | 0 | 102 | 95 | 31 | 32 | 22 | 27 |
| Day 8 | — | — | 99 | 93 | 31 | 33 | 23 | 27 |

| | Mesh Number: Set "b" | | | | | | | |
|---|---|---|---|---|---|---|---|---|
| | M1b | M2b | M3b | M4b | M5b | M6b | M7b | M8b |
| 37° C. BSR, % at | | | | | | | | |
| Day 2 | 90 | 95 | 98 | 100 | 100 | 100 | 90 | 87 |
| Day 4 | 80 | 87 | 93 | 100 | 91 | 99 | — | 75 |
| 50° C. BSR at | | | | | | | | |
| Day 2 | 10 | 50 | 95 | 100 | 37 | 68 | 68 | 53 |
| Day 4 | 0 | 3 | 93 | 100 | 29 | 35 | 25 | 27 |

EXAMPLE 8

Preparation of Composite Coreless Braid

General Method

Composition consisting of components A and B yarns having different degradation profiles (typically one fast degrading and one slow degrading) were constructed using various ratios of A and B to construct a braid sheath or coreless suture. Braided constructions were produced using a 12 carrier vertical axis bobbin braiding machine utilizing 6 carriers for each A and B component. Bobbin placement of the different A and B components in the braiding machine was completed such that a balanced construction was attained. Various combinations were constructed using at least one relatively fast and one relatively slow degrading component with homogenous control constructions. Following braid construction (36 pics/inch) samples were annealed at 80° C. while tensioned under a pre-load of 50 grams for 1 hour. Resultant coreless braids were of diameter range 0.26 mm-0.30 mm. Details of the construction and its effect on the in vitro conditioned properties are noted in Example 9.

EXAMPLE 9

In Vitro Testing of Composite Coreless Braids

Braids made according to teaching of Example 8 were tested following the test methods outlined below to provide the experimental results of the different combinations from yarns made from P1 through P4 copolyesters which, in turn, were made and processed in accordance with the prior art disclosed by one of the present inventors and described in Example 1.

Testing Methods: In vitro conditioned break strength retention (% BSR=max. load @ time point/initial max. load×100) was conducted using a MTS MiniBionix Universal Tester (model 858) equipped with suture grips. Samples were conditioned using a 0.1M solution of buffered sodium phosphate at a 7.2 pH in 15 mL tubes. Tubes were placed in racks and incubated at 37° C. or 50° C. under constant orbital-agitation. Samples were removed at predetermined time points for tensile testing (n=3).

Type of Yarns Used and Sources: All used yarns are multifilaments produced by melt-spinning of P1 and P2 of Example 1 according to the general process outlined in Example 2.

Composition of Tested Braids: These are described in Table V below.

TABLE V

Composition of the Multifilament Yarns Used for Braiding and Tensile Properties of Braided Coreless Sutures Therefrom

| Yarn Composition & Braid Properties | Braid Number: | | | | | | | |
|---|---|---|---|---|---|---|---|---|
| | B1 | B2 | B3 | B4 | B5 | B6 | B7 | B8 |
| Yarn Composition % of yarn derived from | | | | | | | | |
| P1 | 100 | — | — | — | 50 | — | — | 25 |
| P2 | — | 100 | — | — | — | 50 | 50 | 25 |
| P3 | — | — | 100 | — | — | 50 | — | — |
| P4 | — | — | — | 100 | 50 | — | 50 | 50 |
| Braid Properties | | | | | | | | |
| Diameter mm | 0.29 | 0.26 | 0.26 | 0.27 | 0.30 | 0.26 | 0.26 | 0.27 |
| Max. load, N | 38.4 | 29.5 | 28.6 | 31.5 | 31.6 | 23.3 | 28.6 | 29.9 |
| Strength, Kpsi | 84 | 81 | 78 | 80 | 65 | 64 | 78 | 76 |
| Modulus, Kpsi | 1016 | 1013 | 744 | 633 | 453 | 845 | 828 | 721 |
| Elongation, % | 22 | 21 | 46 | 34 | 31 | 23 | 27 | 32 |

Breaking Strength Retention Data of Tested Braid: These data are outlined in Table VI.

TABLE VI

In Vitro Breaking Strength Retention (BSR) of Braided Coreless Sutures

| BSR Data | B1 | B2 | B3 | B4 | B5 | B6 | B7 | B8 |
|---|---|---|---|---|---|---|---|---|
| 37° C. BSR, % at | | | | | | | | |
| Day 6 | 81 | 65 | — | 91 | 66 | 61 | 66 | 57 |
| Day 8 | 63 | 48 | 83 | 87 | 52 | 53 | 53 | — |
| Day 10 | 48 | 32 | 82 | — | 44 | — | — | — |
| Week 2 | 12 | 0 | 78 | 86 | — | 49 | 52 | 52 |
| Week 3 | 0 | — | 73 | — | 45 | — | — | — |
| Week 4 | — | — | — | 81 | — | 50 | 54 | 48 |
| Week 5 | — | — | 68 | 81 | 44 | 38 | — | 47 |
| Week 9 | — | — | 62 | 75 | 42 | 37 | 49 | 45 |
| 50° C. BSR, % at | | | | | | | | |
| Day 2 | 53 | 55 | 86 | — | — | 62 | 65 | — |
| Day 4 | 3 | 0 | 82 | 93 | 51 | — | 57 | 52 |
| Day 6 | 0 | — | — | — | — | 52 | 56 | — |
| Day 8 | — | — | 75 | 90 | 46 | 46 | 56 | 49 |
| Week 2 | — | — | 63 | 89 | 46 | 41 | 52 | 47 |
| Week 3 | — | — | 56 | 81 | 42 | 32 | 49 | 44 |
| Week 4 | — | — | — | 77 | 38 | 28 | 44 | 43 |
| Week 5 | — | — | 37 | 74 | — | 26 | 43 | — |
| Week 9 | — | — | 12 | 39 | 22 | 0 | 7 | 25 |

EXAMPLE 10

Preparation of Composite Jersey Knit Mesh

General Method

Composition consisting of components A and B yarns having different degradation profiles (typically one fast degrading and one slow degrading) were constructed using various ratios of A and B to construct a jersey knit mesh tube. Knit constructions were produced using a single or multiple feed circular knitting machine that resulted in a plied construction of the A and B component. Various combinations were constructed where the ratio of A to B was varied resulting in modulated physicomechanical properties. Knit constructions can be made from multifilament yarn, monofilament yarn, or combinations therefrom. Yarn was typically plied in the desired ratio of A to B prior to knit construction. Knit tubes were annealed by stretching the circular mesh over stainless steel circular mandrels and heat setting the knit construction. In addition, coatings, especially those of hydrophobic nature, were used to improve BSR and thus overall strength during the initial time periods. Details of the construction and resultant in vitro conditioned properties are noted in Example 11.

EXAMPLE 11

In Vitro Testing of Composite Jersey Knit Mesh

Meshes made according to Example 10, using combinations of different yarns (see Table VII), were tested following the test methods described below. The meshes were tested and corresponding results are also shown below (Table VIII).

Testing Methods: In vitro conditioned break strength retention (% BSR=max. load @ time point/initial max. load× 100) was conducted using a MTS MiniBionix Universal Tester (model 858) equipped with a burst test apparatus as detailed in ASTM D3787-01. Samples were conditioned using a 0.1 M solution of buffered sodium phosphate at a 7.2 pH in 50 mL tubes. Tubes were placed in racks and incubated at 37° C. under constant orbital-agitation. Samples were removed at predetermined time points for burst testing (n=3).

Types of Yarns Used and Source: All used yarns are made by melt spinning the specific polymers of Example 1, namely P1, P2, and P3, according to the general procedure of example 2. The used yarns include the following: MG-9 monofilament yarns made by melt spinning of P1; SMC-7 multifilament made by melt spinning of P2; and SMC-22 multifilament yarn made by melt spinning of P3.

Compositions of Tested Jersey Knit Meshes: These are outlined in Table VII.

TABLE VII

Composition of the Multifilament Yarns Used for Knitting Mesh Tubes and Tensile Properties of Composite Meshes Therefrom

| Yarn Composition & Mesh Properties | Mesh Number: | | | |
|---|---|---|---|---|
| | M1 | M2 | M3 | M4 |
| Yarn Composition % of yarn derived from | | | | |
| P1 | 25 | 25 | 50 | 50 |
| P2 | 75 | — | 50 | — |
| P3 | — | 75 | — | 50 |
| Mesh Properties | | | | |
| Max. load, N | 707 | 520 | 536 | 501 |
| Elongation, % | 44 | 49 | 44 | 53 |

Breaking Strength Retention Data of Tested Jersey Knit Meshes: These are outlined in Table VIII.

TABLE VIII

In Vitro Breaking Strength Retention (BSR) of Composite Circular Knit Mesh Tubes

| BSR Data | Mesh Number: | | | |
|---|---|---|---|---|
| | M1 | M2 | M3 | M4 |
| 50° C. BSR, % at | | | | |
| Day 4 | 79 | 67 | 50 | 41 |
| Day 7 | 77 | 67 | 50 | 44 |
| Day 10 | 77 | 67 | 48 | 45 |
| Day 14 | 77 | 67 | 46 | 44 |
| Day 28 | 72 | 62 | 45 | 35 |

EXAMPLE 12

Preparation of Composite Warp Knit Mesh

General Method

Composition consisting of components A and B yarns having different degradation profiles (typically one fast degrading and one slow degrading) were constructed using various ratios of A and B to construct multi-pattern integrated meshes. Knit constructions were produced using a two step process of warping yarn onto beams and constructing meshes using a raschel or tricot knitting machine of the standard art. Various knitting patterns and weight ratios of A to B can and were varied to modulate mechanical properties. Knit constructions can be made from multifilament yarn, monofilament yarn, or combinations therefrom. Knit mesh was annealed at 120° C. for 1 hour while under strain in the wale and course directions. Coating can be applied following annealing to modify in vitro characteristics. Details of the compositions, initial mesh properties and resultant in vitro properties are summarized in Tables IX and X.

EXAMPLE 13

In Vitro Testing of Warp Knit Meshes

The meshes made according to Example 12 were tested using the combination of yarns and test methods described below:

Testing Methods: In vitro conditioned break strength retention (% BSR=max. load @ time point/initial max. load× 100) was conducted using a MTS MiniBionix Universal Tester (model 858) equipped with a burst test apparatus as detailed in ASTM D3787-01. Samples were conditioned using a 0.1M solution of buffered sodium phosphate at a 7.2 pH in 50 mL tubes. Tubes were placed in racks and incubated at 37° C. under constant orbital-agitation. Samples were removed at predetermined time points for burst testing (n=3).

Types of Yarns Used and Source: All used yarns are made by melt-spinning the specific polymers of Example 1, namely, P1 and P2, according to the general procedure of Example 2. The used yarns include the following: MG-9 monofilament yarn made by the melt-spinning of P1; and SMC-7 multifilament yarn made by melt-spinning of P2.

Composition and Construction of Individual Warp Knit Meshes:

WK1: 40/60 MG-9/SMC-7 Percent Weight Ratio Determined by Extraction

Yarn—2-ply 90 denier SMC-7, Single monofilament 0.100 mm diameter MG-9

Knitting process—utilized a single warped beam of SMC-7 and two warped beams of MG-9 on a 24 gauge knitting machine, MG-9 knitted in a standard 2 bar marquisette pattern and SMC-7 knitted in a single bar tricot pattern. All guide bars were threaded 1-in and 1-out.

Annealing was conducted at 120° C. for 1 hour to yield meshes having an area weight of 125 g/m$^2$.

WK2: 30/70 MG-9/SMC-7 Percent Weight Ratio Determined by Extraction

Yarn—2-ply 90 denier SMC-7, Single monofilament 0.100 mm diameter MG-9

Knitting process—utilized two warped beams of SMC-7 and two warped beams of MG-9 on a 24 gauge knitting machine, MG-9 knitted in a standard 2 bar marquisette pattern and SMC-7 knitted in a 2 bar sand-fly net pattern. All guide bars were threaded 1-in and 1-out.

Annealing was completed at 120° C. for 1 hour and the resultant area weight was 165 g/m$^2$.

WK1-C: Annealed WK1 mesh dip coated with an absorbable coating that was prepared by dissolved in acetone at a concentration of 8 g/100 mL. Coating was applied by dip coating and resulting add-on, after drying, was 10% by weight.

Mechanical Property Data of Warp Knit Meshes: These are outlined in Table IX.

TABLE IX

Composition of the Warp Knit Mesh and Tensile Properties of Composite Meshes Therefrom

| Yarn Composition & Mesh Properties | Mesh Number: | | |
|---|---|---|---|
| | WK1 | WK2 | WK1-C |
| Yarn Composition weight % of yarn derived from | | | |
| P1 | 40 | 30 | 40 |
| P2 | 60 | 70 | 60 |
| Mesh Properties | | | |
| Max. burst load, N | 206 | 224 | 202 |
| Elongation at max. load, % | 13 | 18 | 18 |

In Vitro Breaking Strength Retention Data of Warp Knit Meshes: These are outlined in Table X.

TABLE X

In Vitro Breaking Strength Retention (BSR) of Composite Warp Knit Mesh

| BSR Data | Mesh Number: | | |
|---|---|---|---|
| | WK1 | WK2 | WK1-C |
| 37° C. BSR, % at | | | |
| Day 2 | 100 | 100 | 93 |
| Day 4 | 84 | 92 | 87 |
| Day 5 | 90 | 94 | — |
| Day 7 | 73 | 92 | 90 |
| Day 10 | 92 | 94 | 100 |
| Day 14 | 85 | 92 | — |
| Day 21 | 92 | 97 | — |

EXAMPLE 14

Preparation of Composite Sutures

General Method

Composition consisting of components A and B yarns having different degradation profiles (typically one fast degrading and one slow degrading) were constructed using various ratios of A and B to construct ligand structures. Braid constructions can be produced using material A in the core and B as the sheath or B as the core and A as the sheath. In addition, components A and B can be of braid construction consisting of multifilament yarn, monofilament yarn, or combinations therefrom. Monofilament cores can be comprised of a single fiber or multiple fibers. For example, a core can comprise three twisted 0.100 mm monofilaments and utilizing a 2-ply multifilament (70 denier per ply) sheath braided using 12 carriers can physically secure the sheath core interface. Details of the construction and resultant in vitro conditioned properties are noted in Example 15.

EXAMPLE 15

In Vitro Testing of Composite Sutures

Sutures made according to Example 14 using a combination of monofilament and multifilament yarns were tested using the test method outlined below. Test results are outlined in Table XI.

TABLE XI

Composition of the Multifilament and Monofilament Yarns Used for Braiding and Tensile Properties of Composite Sutures Therefrom

| Yarn Composition & Braid Properties | Braid Number: | | | | | |
|---|---|---|---|---|---|---|
|  | CS1 | CS2 | CS3 | CS4 | CS5 | CS6 |
| Yarn Composition weight % of yarn derived from | | | | | | |
| P1 | 100 | — | 25 | 58 | — | — |
| P2 | — | 100 | 75 | 42 | 87 | 87 |
| P3 | — | — | — | — | 13 | 13 |
| Braid Properties | | | | | | |
| Diameter, mm | 0.36 | 0.51 | 0.43 | 0.39 | 0.40 | 0.40 |
| Max. load, N | 46.8 | 62.7 | 40.8 | 41.1 | 39.0 | 35.7 |
| Strength, Kpsi | 67 | 45 | 41 | 50 | 45 | 41 |
| Modulus, Kpsi | 724 | 333 | 390 | 612 | 362 | 330 |
| Elongation, % | 26 | 36 | 29 | 26 | 54 | 51 |

Testing Methods Mechanical data were collected using a MTS MiniBionix Universal Tester (model 858) equipped with suture grips. Samples were tested under initial conditions (n=4).

Types of Yarns Used and Sources: All used yarns are made by melt-spinning the specific polymers of Example 1, namely, P1 and P2, according to the general procedure of Example 2. The used yarns include the following: MG-9 monofilament yarn made by the melt-spinning of P1; and SMC-7 multifilament yarn made by melt-spinning of P2.

Composition and Construction of Individual Sutures:

CS1: MG-9 Multifilament Homogeneous Construction

Yarn—1-ply 51 denier, 4.63 tenacity, 31.6% elongation, 20 yarn count

Braiding process—12 carrier sheath (51.2 pics/in) with 6 carrier core (8.6 pics/in)

Hot Stretching—5% at 110° C.

Annealing—completed at 110° C. under high vacuum for 1 hour

CS2: SMC-7 Multifilament Homogeneous Construction

Yarn—1-ply 74 denier, 4.17 tenacity, 26.7% elongation, 43 yarn count

Braiding process—12 carrier sheath (51.2 pics/in) with 6 carrier core (8.6 pics/in)

Hot Stretching—5% at 110° C.

Annealing—completed at 110° C. under high vacuum for 1 hour

CS3: 25/75 MG-9 Multifilament/SMC-7 Multifilament Percent Weight Ratio

Yarn—SMC-7=1-ply 74 denier, 4.17 tenacity, 26.7% elongation, 43 yarn count

MG-9=1-ply 51 denier, 4.63 tenacity, 31.6% elongation, 20 yarn count

Braiding process—12 carrier sheath (51.2 pics/in) with 6 carrier core (8.6 pics/in)

Hot Stretching—5% at 110° C.

Annealing—completed at 110° C. under high vacuum for 1 hour

CS4: 58/42 MG-9 Multifilament/SMC-7 Multifilament Percent Weight Ratio

Yarn—SMC-7=1-ply 74 denier, 4.17 tenacity, 26.7% elongation, 43 yarn count

MG-9=1-ply 51 denier, 4.63 tenacity, 31.6% elongation, 20 yarn count

Braiding process—12 carrier sheath (51.2 pics/in) with 6 carrier core (8.6 pics/in)

Hot Stretching—5% at 110° C.

Annealing—completed at 110° C. under high vacuum for 1 hour

CS5: 13/87 MG-9 Monofilament/SMC-7 Multifilament Percent Weight Ratio

Yarn—SMC-7=1-ply 84 denier, 3.73 tenacity, 37.3% elongation, 43 yarn count

MG-9=0.100 mm diameter, 120 denier

Braiding process—12 carrier sheath (51.2 pics/in) with 6 carrier core (8.6 pics/in)

Hot Stretching—5% at 110° C.

Annealing—completed at 110° C. under high vacuum for 1 hour

CS6: 13/87 MG-9 Monofilament/SMC-7 Multifilament Percent Weight Ratio

Yarn—SMC-7=1-ply 84 denier, 3.73 tenacity, 37.3% elongation, 43 yarn count

MG-9=0.100 mm diameter, 120 denier

Braiding process—12 carrier sheath (51.2 pics/in) with 6 carrier core (8.6 pics/in)

Hot Stretching—10% at 110° C.

Annealing—completed at 110° C. under high vacuum for 1 hour

Mechanical Properties of Composite Sutures: These are outlined in Table XI above.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An absorbable/biodegradable surgical implant comprising at least first and second fibrous components, the fibrous components having differing absorption profiles and differing strength retention profiles in a biological environment, the first and second fibrous components comprise first and second individual continuous yarns; and wherein the first individual continuous yarn comprises a mixture of about 95/5 (molar) glycolide/ε-caprolactone and the second continuous yarn comprises a mixture of about 84/11/5 (molar) l-lactide/trimethylene carbonate/caprolactone.

2. An absorbable/biodegradable surgical implant as set forth in claim 1 in the form of a braided suture.

3. An absorbable/biodegradable surgical implant as set forth in claim 2 wherein the suture further comprises a coating, the coating comprising an absorbable polymer to improve tie-down properties and minimize tissue drag.

4. An absorbable/biodegradable surgical implant as set forth in claim 1 in the form of a knitted mesh construct for use in hernial repair.

5. An absorbable /biodegradable surgical implant as set forth in claim 4 wherein the mesh further comprises a surface coating, the coating comprising an absorbable polymer to modulate the construct permeability to biological fluids and tissue ingrowth into the construct.

6. An absorbable/biodegradable surgical implant as set forth in claim 1 in the form of a woven mesh construct.

7. An absorbable/biodegradable surgical implant as set forth in claim 6 wherein the mesh further comprises a surface coating, the coating comprising an absorbable polymer to modulate the construct permeability to biological fluids and tissue ingrowth into the construct.

8. An absorbable/biodegradable surgical implant as set forth in claim 1 in the form of a device for use as a tissue-engineered hernial repair patch.

9. An absorbable/biodegradable surgical implant as set forth in claim 1 in the form of a device for use as a tendon, ligament, or vascular graft.

10. An absorbable/biodegradable surgical implant as set forth in claim 1 in the form of a tubular knitted mesh.

11. An absorbable/biodegradable surgical implant as set forth in claim 10 wherein the mesh further comprises a thin absorbable film insert.

12. An absorbable/biodegradable surgical implant as set forth in claim 11 wherein the mesh and the film insert are in the form of a compressed, three- layer sheet construct for use in hernial repair.

13. An absorbable/biodegradable surgical implant as set forth in claim 12 wherein the three-layer sheet construct further comprises an absorbable coating.

14. An absorbable/biodegradable surgical implant as set forth in claim 1 further comprising an absorbable polyester coating comprising a bioactive agent, the bioactive agent selected from the group consisting of antimicrobial agents, analgesic agents antineoplastic agents, anti-inflammatory agents, and cell growth promoters.

15. An absorbable/biodegradable surgical implant as set forth in claim 1 in the form of a coated or uncoated suture comprising a monofilament core and a braided sheath.

16. An absorbable/biodegradable surgical implant comprising at least first and second fibrous components, the fibrous components having differing absorption profiles and differing strength retention profiles in a biological environment, the first and second fibrous components comprising first and second differing individual continuous yarns; and
wherein the first individual continuous yarn comprises a mixture of about 95/5 (molar) glycolide/$\epsilon$-caprolactone and the second continuous yarn comprises a mixture of about 88/12 (molar)l-lactide/trimethylene carbonate.

17. An absorbable/biodegradable surgical implant as set forth in claim 16 in the form of a suture, wherein the suture comprises a core derived from the first continuous yarn and a sheath derived from the second continuous yarn, wherein the first continuous yarn and the second continuous yarn have differing absorption profiles and differing strength retention profiles.

18. An absorbable/biodegradable surgical implant as set forth in claim 16 in the form of a coated or uncoated jersey knit mesh.

19. An absorbable/biodegradable surgical implant as set forth in claim 16 in the form of a coated or uncoated wrap knit mesh.

20. An absorbable/biodegradable surgical implant as set forth in claim 16 in the form of a coated or uncoated woven mesh.

21. An absorbable/biodegradable surgical implant as set forth in claim 16 in the form of a device for hernial repair, vascular tissue repair, producing vascular grafts or tissue engineering.

22. An absorbable/biodegradable surgical implant as set forth in claim 16 further comprising a coating comprising an absorbable polyester having a melting temperature of less than 100° C.

23. An absorbable/biodegradable surgical implant as set forth in claim 22 wherein the coating comprises at least one bioactive agent selected from the group consisting of antimicrobial agents, anti-inflammatory agents, antineoplastic agents, anesthetic agents, and growth promoting agents.

24. An absorbable/biodegradable surgical implant as set forth in claim 16 wherein the individual yarns are plied, braided and subsequently knitted or woven into a mesh construct.

* * * * *